(12) United States Patent
Keppler

(10) Patent No.: US 7,122,643 B2
(45) Date of Patent: Oct. 17, 2006

(54) CYTOSTATIC LANTHANUM COMPOUNDS

(75) Inventor: Bernhard Keppler, Hockenheim (DE)

(73) Assignee: Faustus Forschungs Cie. Translational Cancer Research GmbH, Leipzig (DE)

( * ) Notice: Subject to any disclaimer, the term of this patent is extended or adjusted under 35 U.S.C. 154(b) by 52 days.

(21) Appl. No.: 10/773,823

(22) Filed: Feb. 6, 2004

(65) Prior Publication Data

US 2004/0176346 A1 Sep. 9, 2004

Related U.S. Application Data

(63) Continuation of application No. PCT/EP02/08770, filed on Aug. 6, 2002.

(30) Foreign Application Priority Data

Aug. 6, 2001 (DE) .............................. 101 38 538

(51) Int. Cl.
*C07F 5/00* (2006.01)
(52) U.S. Cl. ...................... 534/15; 424/1.11; 424/1.65; 424/9.1; 514/188
(58) Field of Classification Search .................... 546/1; 534/15; 424/1.11, 1.65, 9.1; 514/188
See application file for complete search history.

(56) References Cited

OTHER PUBLICATIONS

Foster, R.J., et al., "Complexes of 1,8-Naphthridines, X. Complexes of 1,8-Naphthridine with Rare Earth Nitrates", *Inorg. Chimica. Acta*, vol. 6, No. 3., pp. 371-375 (1972).
Charpentier, L.J., et al., "Observations on the Rare Earths—LXXXIV—The Preparation and Properties of 1,2-Propanediamine Complexes", *J. inorg. nucl. Chem.*, vol. 32, pp. 3575-3584.
Roesky, P.W., et al. "Aminotroponimines as Ligands for Yttrium and Lanthanide Complexes", *Institut für Anorganische Chemic*, vol. 130, No. 7, pp. 859-862 (1997).
Golub, A.M., et al., "Synthesis and Properties of bipyridne and phenanthroline complexes of selenocyanates of the lanthanides", *Zh. Obsch. Khim*, vol. 39, No. 6, pp. 1382-1387 (1969), Abstract Only.
Bisi, C.C., "Ethylenediamine Complexes of Rare-Earth Trichlorides". *Inorganica Chimica Acta*, vol. 3, No. 4, pp. 660-662 (1969).
Dutt, N.K., et al., "Chemistry of Lanthanons—XXXII—Malondihydrazide Complexes of Lanthanides", *J. inorg. nucl. Chem.*, vol. 33, pp. 4185-4189 (1971).
Patil, B.K., et al. "Preparation and Characterization of Orthophenylenediamine Complexes of Lathanides", Dept. of Chemistry, Visvesvaraya Regional College of Engineering, vol. 45, No. 19, pp. 686-688 (1976).

Eremin, Y.G., et al., "On three-component complexes of yttrium and rare earth elements with 2,2'-bipyridine and o-phenanthroline", *Zh. Obsch. Khim.*, vol. 21, No. 2, pp. 387-394_(1976), Abstract Only.
Mohan, M., et al., "Synthesis and magnetic and spectral properties of some lanthanide(III) chelates of pyridine-2-aldoxime", *Gazzetta Chimica Italiana*, Vo. 110, pp. 293-299 (1980).
Komiyama, M., et al., "Molecular Design of Artificial Enzymes which Selectively Hydrolyze Nucleic Acids—Novel Tools for Future Biotechnology and Cancer Therapy", *Journal of the Faculty of Engineering, Univ. of Tokyo*, vol. 42, No. 2, pp. 143-154 (1993).
Russell J. Foster et al., "Complexes of 1,8-naphthyridines. X Complexes of 1,8-naphthyridine with rare earth nitrates", *Chemical Abstracts*, vol. 77, No. 26, Abstract 172097t (1972).
Linda J. Charpentier et al., "Rare Earths. LXXXIV. Preparation and properties of 1,2-propanediamine complexes", *Chemical Abstracts*, vol. 74, No. 6, Abstract 27594m (1971).
Peter W. Roesky, "Aminotroponimines as Ligands for Yttrium and Lanthanide Complexes", *Chem. Ber./Recueil*, vol. 130, pp. 859-862, (1997).

*Primary Examiner*—Dameron L. Jones
(74) *Attorney, Agent, or Firm*—Akin Gump Strauss Hauer & Feld, LLP

(57) ABSTRACT

Lanthanum compounds are provided having general formulas (I) $R_n^{i+}Y_i^{n-}$ and (II) $R_b^+Y_b^-$ which may be used as medicaments in the prophylaxis and/or treatment of cancer diseases. In formula (I), R is a group of general formula (A):

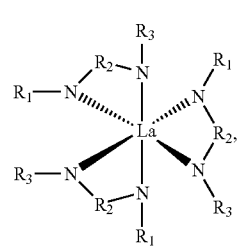

(A)

and in general formula (II) $R_b$ is a group of general formula (B):

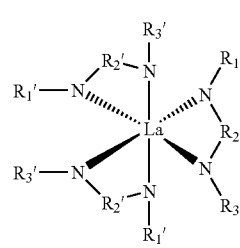

(B)

7 Claims, No Drawings

CYTOSTATIC LANTHANUM COMPOUNDS

CROSS-REFERENCE TO RELATED APPLICATIONS

This application is a continuation of International Application No. PCT/EP02/08770, filed Aug. 6, 2002, and the disclosure of which is incorporated herein by reference.

BACKGROUND OF THE INVENTION

This invention relates to lanthanum compounds and their application as medicaments for the prevention, prophylaxis and/or treatment of cancer diseases.

The object of this invention is to provide a compound which exhibits high effectiveness in the treatment of cancer diseases.

BRIEF SUMMARY OF THE INVENTION

This invention provides a compound of general formula (I)

$$R_n^{i+} Y_i^{n-} \quad (I),$$

wherein R is a group of general formula (A):

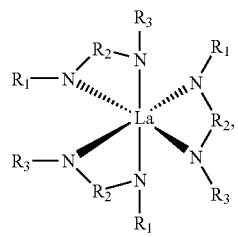

(A)

wherein $R_1$ and $R_3$ are independently selected from the substituted and unsubstituted group consisting of $C_1$–$C_{10}$-alkyl, $C_3$–$C_6$-cycloalkyl, $C_3$–$C_6$-cycloalkenyl, $C_2$–$C_{10}$-alkenyl, $C_6$–$C_{14}$-aryl and a heterocycle, and hydrogen;

$R_2$ is selected from the substituted and unsubstituted group consisting of $C_1$–$C_6$-alkylene, $C_3$–$C_6$-cycloalkylene, $C_3$–$C_6$-cycloalkenylene, $C_2$–$C_6$-alkenylene, $C_6$–$C_{14}$-arylene and a heterocycle;

$R_1$ and $R_2$ and/or $R_2$ and $R_3$ can form an heterocycle optionally containing further nitrogen atoms;

Y is a physiologically compatible anion;

i and n are independently natural numbers $\geq 1$, and physiologically compatible addition salts, provided that R is not:

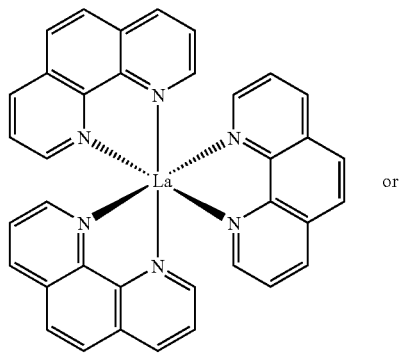 or

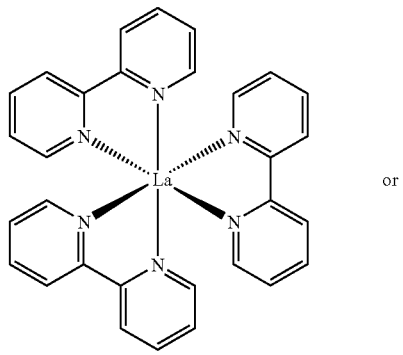 or

and that if Y is $NO_3^-$, R is not

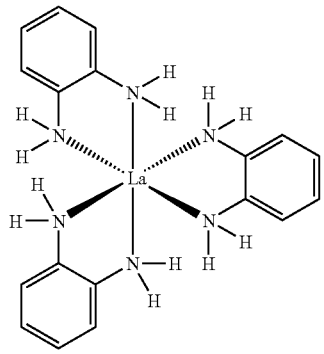

and that if Y is $NO_3^-$, $ClO_4^-$ or $Cl^-$, R is not

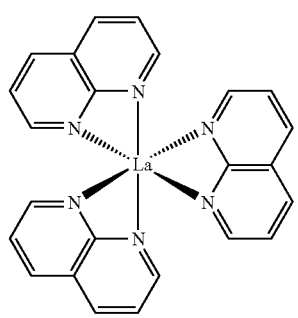

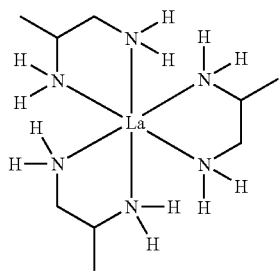

A medicament containing a compound having general formula (I) is also provided by the invention.

DETAILED DESCRIPTION OF THE INVENTION

More specifically, the object of the invention is solved by a compound of the general formula (I)

$$R_n^{i+} Y_i^{n-} \quad (I),$$

where R is a group of the general formula (A)

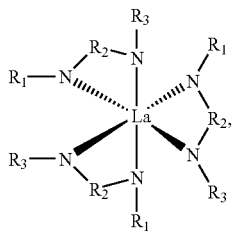

(A)

where $R_1$ and $R_3$ are selected independently of one another from the group consisting of $C_1$–$C_{10}$-alkyl, $C_3$–$C_6$-cycloalkyl, $C_3$–$C_6$-cycloalkenyl, $C_2$–$C_{10}$-alkenyl, $C_6$–$C_{14}$-aryl and a heterocycle, which can in each case be substituted or unsubstituted, and hydrogen;

$R_2$ is selected from the group consisting of $C_1$–$C_6$-alkylene, $C_3$–$C_6$-cycloalkylene, $C_3$–$C_6$-cycloalkenylene, $C_2$–$C_6$-alkenylene, $C_6$–$C_{14}$-arylene and a heterocycle, which can in each case be substituted or unsubstituted;

and $R_1$ and $R_2$ and/or $R_2$ and $R_3$ can form a heterocycle which, optionally, where applicable, can contain further nitrogen atoms;

Y is a physiologically compatible anion;

i and n are independent of one another and are natural numbers $\geq 1$, and physiologically compatible addition salts, provided that R is not:

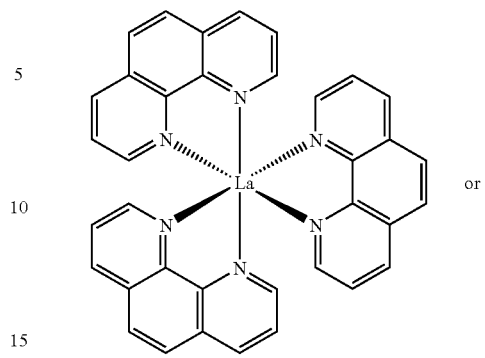

or

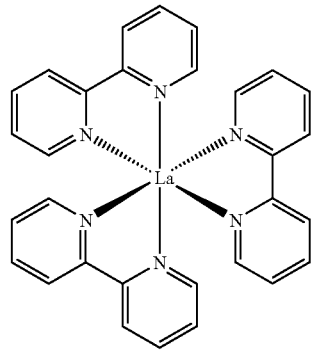

or

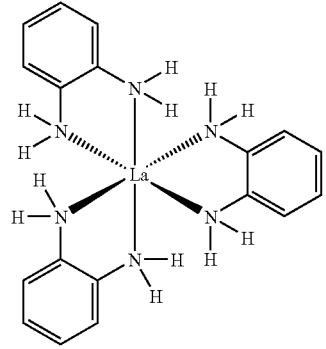

In a preferred embodiment $R_1$ and/or $R_3$ are $C_1$–$C_5$-alkyl, in particular methyl, ethyl or propyl. Also, $R_1$ and/or $R_3$ are preferably cyclobutyl, cyclopropyl, cyclobutenyl or cyclopropenyl and in particular cyclopentyl, cyclohexyl, cyclopentenyl or cyclohexenyl, or $C_2$–$C_5$-alkenyl, in particular ethenyl, propenyl or butenyl. Furthermore, $R_1$ and/or $R_3$ can be benzyl or pyridyl.

$R_2$ is preferably $C_1$–$C_5$-alkylene, in particular methylene, ethylene or propylene. Also, $R_2$ is preferably cyclobutylene, cyclopropylene, cyclopentylene, cyclohexylene, cyclopentenylene or cyclohexenylene or $C_2$–$C_5$-alkenylene, in particular ethenylene, propenylene or butenylene. Furthermore, $R_2$ can be benzylene or pyridylene.

$R_1$, $R_2$ and/or $R_3$ can be substituted by hydroxyl, amino, —$SO_3H$, halogen, $C_1$–$C_4$-alkyl, $C_2$–$C_4$-alkenyl, $C_3$–$C_6$-cycloalkyl, $C_3$–$C_6$-cycloalkenyl, $C_1$–$C_6$-aryl, $C_1$–$C_4$-alkoxy, $C_1$–$C_4$-alkoxy-$C_1$–$C_4$-alkylene, $C_1$–$C_4$-alkylmercapto, $C_1$–$C_4$-alkylmercapto-$C_1$–$C_4$-alkylene, formyl, carboxyl, $C_1$–$C_4$-alkoxycarbonyl, $C_1$–$C_4$-alkoxycarbonyl-$C_1$–$C_4$-alkylene, di-$C_1$–$C_4$-alkylamino, di-$C_1$–$C_4$-alkylamino-$C_1$–$C_4$-alkylene, di-$C_1$–$C_4$-alkylaminocarbonyl, di-$C_1$–$C_4$-alkylaminocarbonyl-$C_1$–$C_4$-alkylene, preferably halogen and especially methyl, ethyl or propyl, in particular if $R_1$ and $R_2$, and/or $R_2$ and $R_3$ form a heterocycle.

In another preferred embodiment "i" is the number 3 and/or "n" is the number 1.

Furthermore, in the general formula (I), Y is preferably a metal halogen, a halogen, a pseudohalogen, $HCO_3$ or R'COO, where R' is $C_1$–$C_6$-alkyl, $C_2$–$C_6$-alkenyl or aryl, which in each case can be substituted or unsubstituted. In particular Y is SCN.

Organic or inorganic addition salts can be formed with the following anions: chloride, bromide, phosphate, carbonate, nitrate, perchlorate, sulphate, citrate, lactate, tartrate, maleate, fumarate, mandelate, benzoate, ascorbate, cinnamate, glycollate, methanesulphonate, formiate, malonate, naphthaline-2-sulphonate, salicylate and/or acetate.

As possible cations H+, sodium and/or potassium cations can be used.

Furthermore, the object of this invention is solved by a medicament containing a compound of the general formula (I)

  (I), where R is a group of the general formula (A)

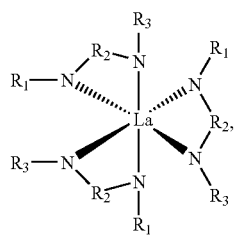  (A)

where $R_1$ and $R_3$ are independently selected from the group consisting of $C_1$–$C_{10}$-alkyl, $C_3$–$C_6$-cycloalkyl, $C_3$–$C_6$-cycloalkenyl, $C_2$–$C_{10}$-alkenyl, $C_6$–$C_{14}$-aryl and a heterocycle, which can in each case be substituted or unsubstituted, and hydrogen;

$R_2$ is selected from the group consisting of $C_1$–$C_6$-alkylene, $C_3$–$C_6$-cycloalkylene, $C_3$–$C_6$-cycloalkenylene, $C_2$–$C_6$-alkenylene, $C_6$–$C_{14}$-arylene and a heterocycle, which can in each case be substituted or unsubstituted;

and $R_1$ and $R_2$ and/or $R_2$ and $R_3$ can form a heterocycle which, optionally, where applicable, can contain additional nitrogen atoms;

Y is a physiologically compatible anion;

i and n are independent of one another and are natural numbers $\geq 1$, and physiologically compatible addition salts.

For the medicament, containing a compound of the general formula (I), with regard to the groups $R_1$, $R_2$, $R_3$, Y, i and n, the same embodiments are preferred as presented above for the compound according to the invention.

In the preferred embodiments the group R of the general formula (A) can be selected from:

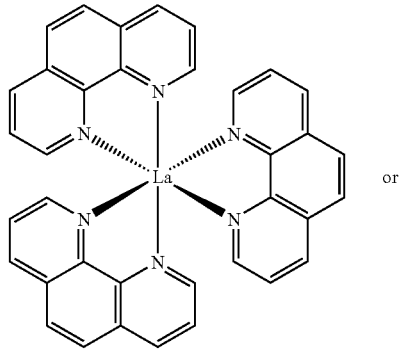 or

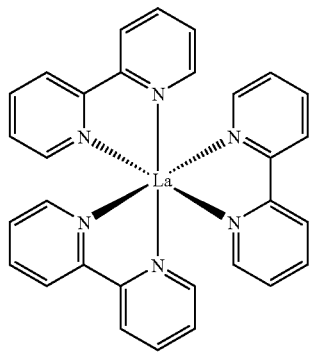

The compound according to the invention can be used for the prophylaxis and/or treatment of cancer diseases.

In another embodiment the object is solved by a compound of the general formula (II)

  (II), where $R_b$ is a group of the general formula (B)

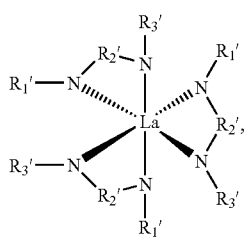  (B)

where $R_1'$ and $R_3'$ are independently selected from the group consisting of $C_1$–$C_{10}$-alkyl, $C_3$–$C_6$-cycloalkyl, $C_2$–$C_{10}$-alkenyl, $C_6$–$C_{14}$-aryl, and a heterocycle, which can be substituted or unsubstituted, and hydrogen;

$R_2'$ is selected from the group consisting of $C_1$–$C_6$-alkylene, $C_3$–$C_6$-cycloalkylene, $C_2$–$C_6$-alkenylene, $C_6$–$C_{14}$-arylene and a heterocycle, which in each case can be substituted or unsubstituted;

and $R_1'$ and $R_2'$ or $R_2'$ and $R_3'$ can form a heterocycle which can, optionally, where applicable, contain further nitrogen atoms;

and $Y_b$ is a metal halogen, a halogen, a pseudohalogen, $HCO_3$ or R'COO, where R' is $C_1$–$C_6$-alkyl, $C_2$–$C_6$-alkenyl or aryl, which in each case can be substituted or unsubstituted.

In preferred embodiments the group $R_b$ of the general formula (B) can be selected from:

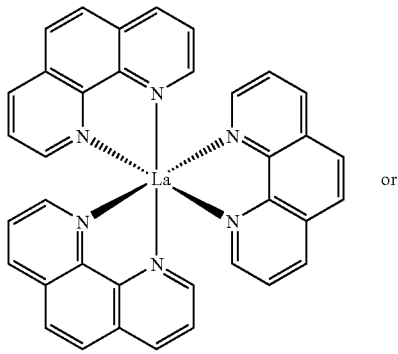

or

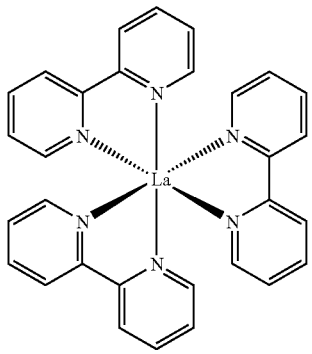

$R_1'$ and $R_3'$ are preferably $C_1$–$C_5$-alkyl, especially methyl, ethyl, or propyl. Also, $R_1'$ and $R_3'$ are preferably cyclobutyl, cyclopropyl or $C_2$–$C_5$-alkenyl, in particular ethenyl, propenyl or butenyl. Furthermore, $R_1'$ and $R_3'$ can be benzyl or pyridyl.

$R_1'$ and $R_3'$ can be substituted by methyl, ethyl or propyl, in particular when $R_1'$ and $R_2'$ or $R_2'$ and $R_3'$ form a heterocycle.

$R_2'$ is preferably $C_1$–$C_5$-alkylene, in particular methylene, ethylene or propylene. Also, $R_1'$ and $R_3'$ are preferably cyclobutylene, cyclopropylene, or $C_2$–$C_5$-alkenylene, in particular ethenylene, propenylene or butenylene. Furthermore $R_2'$ can be benzylene or pyridylene.

$R_2'$ can be substituted by methyl, ethyl or propyl, in particular when $R_1'$ and $R_2'$ or $R_2'$ and $R_3'$ form a heterocycle.

Furthermore, $Y_b$ in the general formula (II) is preferably SCN.

Also, the object of this invention is solved by a medicament which contains the compound according to the invention. The compound according to the invention can be used for the prevention, prophylaxis and/or treatment of cancer diseases.

In the following the medicament containing the compound according to the invention is described in more detail.

The medicament according to the invention is primarily administered intravenously, but also intramuscularly, intraperitoneally, subcutaneously or perorally. External application is also possible. Preferably, it is administered by intravenous injection or by intravenous infusion.

The medicament is manufactured according to known methods, whereby the compound according to the invention as such or, where applicable, is used in combination with suitable pharmaceutical carrier substances. If the medicament according to the invention contains pharmaceutical carrier substances as well as the active substance, the content of active substance in this mixture is about 0.1 to 99.5, preferably about 0.5 to 95% by weight of the total mixture.

The medicament according to the invention can be applied in any suitable formulation with the prerequisite that the establishment and maintenance of a sufficient level of active substance is ensured. This can, for example, be achieved by the oral or parenteral administration in suitable doses. Advantageously, the pharmaceutical preparation of the active substance is provided in the form of standard doses which are matched to the desired administration. A standard dose can, for example, be a tablet, dragee, capsule, suppository or a measured volume of a powder, granulate, solution, emulsion or suspension.

A "standard dose" for the purposes of this invention is taken to mean a physically determined unit which contains an individual quantity of the active constituent in combination with a pharmaceutical carrier substance and its content of active substance corresponds to a fraction or multiple of a therapeutic single dose. A single dose preferably contains the quantity of active substance which is administered during an application and which normally corresponds to a whole, half, third or quarter of the daily dose. If only a fraction, such as half or quarter of the standard dose is needed for a single therapeutically administered dose, then the standard dose is advantageously divisible, e.g. in the form of a tablet with a dividing groove.

The medicaments according to the invention can, if they are available in standard doses and intended for application, e.g. on persons, contain about 0.1 to 500 mg, preferably about 10 to 200 mg and particularly about 50 to 150 mg of active substance.

Generally in human medicine, the active substance(s) are administered in a daily dose of about 0.1 to 5, preferably about 1 to 3 mg/kg of body weight, where necessary in the form of a number of, preferably about 1 to 3, single intakes for achieving the desired results. A single intake contains the active substance(s) in quantities of about 0.1 to 5, preferably about 1 to 3 mg/kg of body weight. With oral treatment similar dosages can be applied.

The therapeutic administration of the medicament according to the invention can occur about 1 to 4 times daily at specified or varying time points, e.g. in each case before meals and/or in the evening. However, it may be necessary to deviate from the quoted dosages depending on the type, body weight and age of the individual to be treated, the type and severity of the disease, the type of preparation and the application of the medicament as well as the time period or interval within which the administration occurs. Consequently, in some cases it may be sufficient to use less than the amount of active substance mentioned above, whereas in other cases the above listed quantity of active substance must be exceeded. It may also be practicable to administer the medicaments only once or at intervals of a number of days.

The specification of the necessary optimum dosage and type of application of the active substances can be made by any specialist based on his specialist knowledge.

The medicaments according to the invention normally comprise the compounds according to the invention and non-toxic, pharmaceutically compatible medication carriers, which as additive or dilution agents, are employed, for example, in solid, semi-solid or liquid form or as a means of enclosure, for example in the form of a capsule, a tablet coating, a bag or another container for the therapeutically active constituent. A carrier substance may, for example, act as an agent for the ingestion of the medicament by the body, as a formulation agent, sweetener, taste modifier, colorant or as a preservative.

For oral application, for example, tablets, dragees, hard and soft capsules, for example of gelatine, dispersible powder, granulate, aqueous and oily suspensions, emulsions, solutions and syrups can be employed.

Tablets can contain inert dilution agents, e.g. calcium carbonate, calcium phosphate, sodium phosphate or lactose; granulation and distributing agents, e.g. maize starch or alginate; binding agents, e.g. starch, gelatine or arabine; and lubricating agents, e.g. aluminium or magnesium stearate, talcum or silicone oil. They can additionally be provided with a coating which is produced such that it causes delayed release and resorption of the medicament in the gastro-intestinal tract, so that, for example, improved compatibility, assimilation or retardation is achieved. Gelatine capsules may contain the pharmaceutical substance mixed with a solid, e.g. calcium carbonate or kaolin or an oily dilution agent, e.g. olive, peanut or paraffin oil.

Aqueous suspensions can contain suspension agents, e.g. sodium carboxymethyl cellulose, methyl cellulose, hydroxypropyl cellulose, sodium alginate, polyvinyl pyrrolidon, traganth rubber or arabine; dispersant or wetting agents, e.g. polyoxyethylene stearate, heptadeca-ethylene-oxycatanol, polyoxyethylene sorbitol-monooleate, or lecithin; preservatives, e.g. methyl- or propylhydroxy-benzoate; taste modifiers; sweeteners, e.g. saccharose, lactose, sodium cyclamate, dextrose, invert sugar syrup.

Oily suspensions may be, for example, peanut, olive, sesame, coconut or paraffin oil and thickening agents, such as bees wax, high melting point wax or cetyl alcohol; also sweeteners, taste modifiers and antioxidants.

Powder and granulates dispersible in water may contain the compound according to the invention in a mixture with dispersing, wetting and suspension agents, e.g. those mentioned above as well as with sweeteners, taste modifiers and colorants.

Emulsions can, for example, contain olive, peanut or paraffin oil as well as emulsifying agents such as arabine, traganth rubber, phosphatides, sorbitan monooleate, polyoxyethylene sorbitan monooleate and sweeteners and taste modifiers.

Aqueous solutions can contain preservatives, e.g. methyl- or propylhydroxybenzoates, thickening agents; taster modifiers; sweeteners, e.g. saccharose, lactose, sodium cyclamate, dextrose, invert sugar syrup as well as taste modifiers and colorants.

For the parenteral application of pharmaceutical substances sterile injectable aqueous solutions, isotonic salt solutions or other solutions can be used.

The invention will be further illustrated in accordance with the following non-limiting examples:

EXAMPLE 1

Synthesis of [tris(1,10-phenantrolin)lanthanum(III)] trithiocyanate

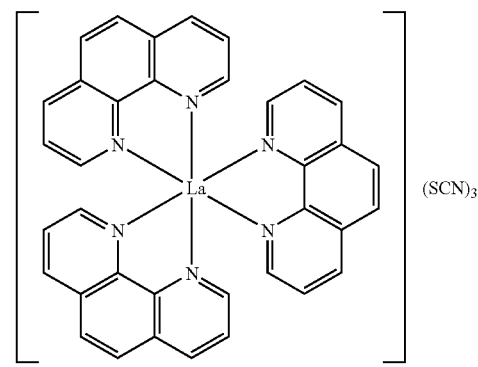

The manufacture of [tris(1,10-phenantrolin)lanthanum (III)]trithiocyanate was performed bycombining lanthanum trichloride hexahydrate ($LaCl_3 \cdot 6H_2O$) in 0.05 M of ethanolic solution with potassium thiocyanate (KSCN) in 0.053 M ethanolic solution in a molar ratio of 1:4. After filtering off the potassium chloride precipitate produced, the filtrate was slowly added drop by drop while stirring to a 0.1 M ethanolic 1,10-phenatrolinmonohydrate solution. The fine crystalline product produced was filtered, washed a number of times with ethanol and dried over calcium sulphate in a vacuum.

EXAMPLE 2

Cytostatic activity of [tris(1,10-phenantrolin)lanthanum (III)]trithiocyanate

Good effectiveness with the following parameters was found in the 48-h sulphurhodamine B-assay on over 50 human tumour cell lines:

| Mean $GI_{50}$: | 1.29 µmol/l | 1.10 µg/ml |
| Mean TGI: | 13.2 µmol/l | 11.3 µg/ml |
| Mean $LC_{50}$: | 55.0 µmol/l | 46.9 µg/ml |

Above average activities were observed here in particular on some melanoma and kidney cell carcinoma cell lines.

In the propidium iodide assay on 13 human tumour xenografts and 10 human tumour cell lines a good cytostatic activity was also found with the following parameters:

| Mean $IC_{50}$: | 4.21 µmol/l | 3.60 µg/ml |
| Mean $IC_{70}$: | 7.90 µmol/l | 6.74 µg/ml |
| Mean $IC_{90}$: | 14.2 µmol/l | 12.1 µg/ml |

Here a selectivity for prostate and colorectal carcinoma was observed. Above average activities were also found on two mammary carcinoma cell lines (MCF7, MDA468A) and a parvicellular bronchial carcinoma cell line (DMS 114) as well as on one each of melanoma, ovarian, kidney cell and non-parvicellular bronchial carcinoma xenografts.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:
1. A compound of general formula (I)

$$R_n^{i+}Y_i^{n-} \quad (I),$$

wherein R is a group of general formula (A):

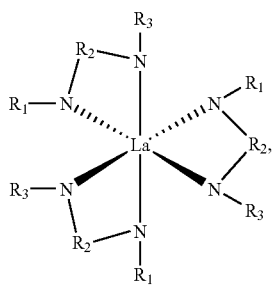

(A)

wherein
- $R_1$ and $R_3$ are independently selected from the substituted and unsubstituted group consisting of $C_1$–$C_{10}$-alkyl, $C_3$–$C_6$-cycloalkyl, $C_3$–$C_6$-cycloalkenyl, $C_2$–$C_{10}$-alkenyl, $C_6$–$C_{14}$-aryl and a heterocycle, and hydrogen;
- $R_2$ is selected from the substituted and unsubstituted group consisting of $C_1$–$C_6$-alkylene, $C_3$–$C_6$-cycloalkylene, $C_3$–$C_6$-cycloalkenylene, $C_2$–$C_6$-alkenylene, $C_6$–$C_{14}$-arylene and a heterocycle;
- $R_1$ and $R_2$ and/or $R_2$ and $R_3$ can form an heterocycle optionally containing further nitrogen atoms;
- Y is a physiologically compatible anion;
- i and n are independently natural numbers $\geq 1$, and physiologically compatible addition salts, provided that R is not:

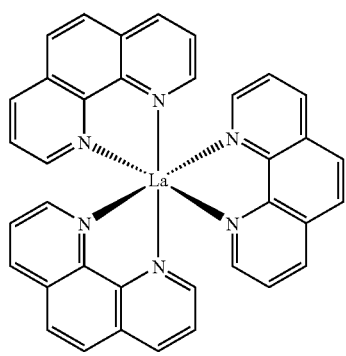

or

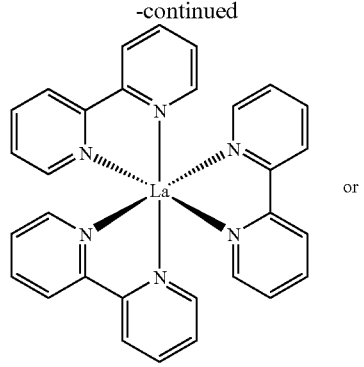

and that if Y is $NO_3^-$, R is not

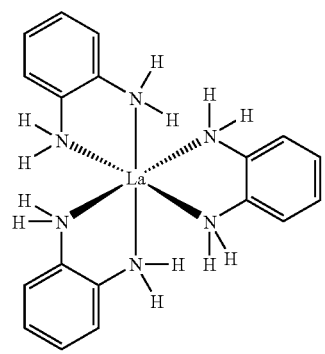

and that if Y is $NO_3^-$, $ClO_4^-$ or $Cl^-$, R is not

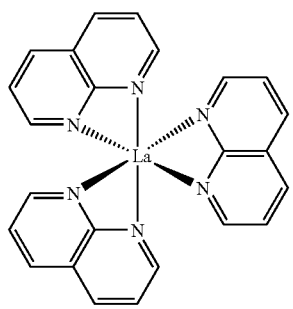

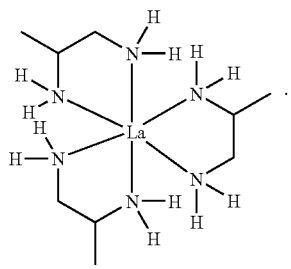

2. The compound according to claim 1, wherein Y in general formula (I) is SCN.

3. A method of treating a cancer disease comprising administering to a subject having a cancer disease a medicament containing a pharmaceutical carrier and a compound of general formula (I)

$$R_n^{i+}Y_i^{n-} \quad (I),$$

wherein R is a group of the general formula (A)

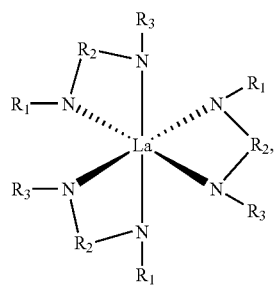

(A)

wherein $R_1$ and $R_3$ are independently selected from the substituted and unsubstituted group consisting of $C_1$–$C_{10}$-alkyl, $C_3$–$C_6$-cycloalkyl, $C_3$–$C_6$-cycloalkenyl, $C_2$–$C_{10}$-alkenyl, $C_6$–$C_{14}$-aryl and a heterocycle, and hydrogen;

$R_2$ is selected from the substituted and unsubstituted group consisting of $C_1$–$C_6$-alkylene, $C_3$–$C_6$-cycloalkylene, $C_3$–$C_6$-cycloalkenylene, $C_2$–$C_6$-alkenylene, $C_6$–$C_{14}$-arylene and a heterocycle;

$R_1$ and $R_2$ and/or $R_2$ and $R_3$ can form an heterocycle optionally containing further nitrogen atoms;

Y is a physiologically compatible anion;

i and n are independently natural numbers $\geq 1$, and physiologically compatible addition salts;

the compound of general formula (I) being present in an amount effective to treat a cancer disease.

4. The method according to claim 3, wherein R in general formula (I) is:

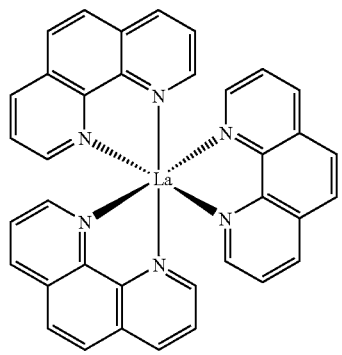

5. The method according to claim 3, wherein R in general formula (I) is:

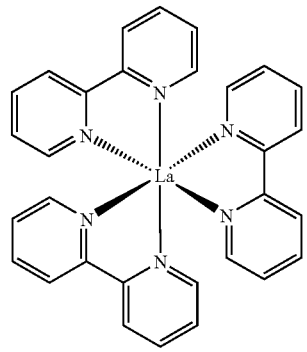

6. A method of preventing or treating cancer diseases comprising administering to a subject having a cancer disease a compound of general formula (I) according to claim 1.

7. A method of treating a cancer disease comprising administering to a subject having a cancer disease a compound of general formula (I) according to claim 2.

* * * * *